(12) United States Patent
Ou et al.

(10) Patent No.: US 10,271,835 B2
(45) Date of Patent: Apr. 30, 2019

(54) DEVICE FOR SURGICAL LIGATION

(71) Applicants: National Cheng Kung University, Tainan (TW); National Cheng Kung University Hospital, Tainan (TW)

(72) Inventors: Chien-Hui Ou, Tainan (TW); Huei-Hua Hsiao, Tainan (TW); Tai-Ho Li, Tainan (TW)

(73) Assignees: NATIONAL CHENG KUNG UNIVERSITY, Tainan (TW); NATIONAL CHENG KUNG UNIVERSITY HOSPITAL, Tainan (TW)

( * ) Notice: Subject to any disclaimer, the term of this patent is extended or adjusted under 35 U.S.C. 154(b) by 151 days.

(21) Appl. No.: 15/239,882

(22) Filed: Aug. 18, 2016

(65) Prior Publication Data
US 2017/0238921 A1  Aug. 24, 2017

(30) Foreign Application Priority Data
Feb. 18, 2016  (TW) .............................. 105104824 A

(51) Int. Cl.
*A61B 17/04* (2006.01)
*A61B 34/00* (2016.01)
(Continued)

(52) U.S. Cl.
CPC .......... *A61B 17/0469* (2013.01); *A61B 34/70* (2016.02); *A61B 34/30* (2016.02);
(Continued)

(58) Field of Classification Search
CPC ..... A61B 17/0469; A61B 34/70; A61B 34/30; A61B 2017/00398; A61B 2017/00424; A61B 2017/0474; A61B 2017/0475; A61B 2017/0477; A61B 17/0482; A61B 17/0483; A61B 17/0485
See application file for complete search history.

(56) References Cited

U.S. PATENT DOCUMENTS 5,766,186 A * 6/1998 Faraz ................. A61B 17/0469
  606/145
9,125,645 B1 * 9/2015 Martin ............... A61B 17/0469
(Continued)

OTHER PUBLICATIONS

Chien-Hui Ou and Huei-Hua Hsiao, "One hand controlled automatic suture ligation and closure device for blood vessels and tissues", TUA2015, 37th Annual Meeting of Taiwan Urological Association (Aug. 22, 2015), Taiwan, 10 pages.

*Primary Examiner* — David C Eastwood
*Assistant Examiner* — Erich Herbermann
(74) *Attorney, Agent, or Firm* — Bacon & Thomas, PLLC

(57) ABSTRACT

A device for surgical ligation is provided, which comprises: a housing, where a pulling portion is provided therein; and an opening portion provided at one end of the housing and connected to the pulling portion, where a line delivery element is provided therein. The line delivery element comprises: a first arc unit having a first coupling portion and a slot thereon; a second arc unit having a second coupling portion corresponding to the first coupling portion; and a gear assembly comprising a plurality of gears engaging with each other, wherein a first gear is engaged with the pulling portion while a second gear is engaged with the second arc unit.

12 Claims, 13 Drawing Sheets

(51) Int. Cl.
    *A61B 17/00*     (2006.01)
    *A61B 34/30*     (2016.01)
(52) U.S. Cl.
    CPC ............ *A61B 2017/00398* (2013.01); *A61B 2017/00424* (2013.01); *A61B 2017/0474* (2013.01)

(56) References Cited

U.S. PATENT DOCUMENTS

| | | | | |
|---|---|---|---|---|
| 2003/0216756 | A1* | 11/2003 | Klein | A61B 17/0057 606/144 |
| 2009/0088778 | A1* | 4/2009 | Miyamoto | A61B 17/0401 606/144 |
| 2011/0202074 | A1* | 8/2011 | Talmo | A61B 17/0401 606/145 |
| 2016/0367243 | A1* | 12/2016 | Martin | A61B 17/0469 |

* cited by examiner

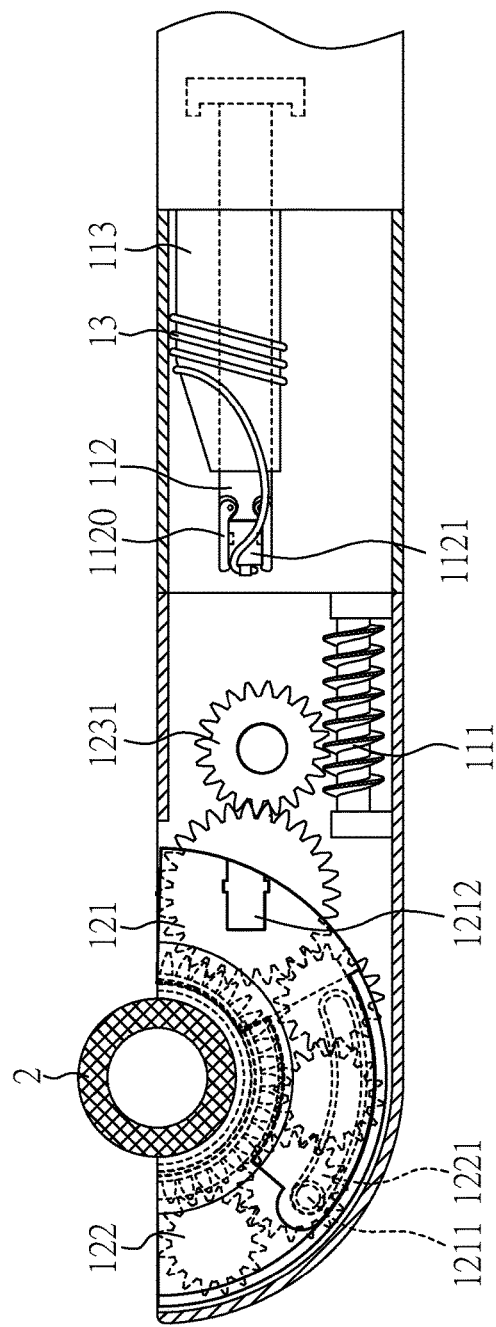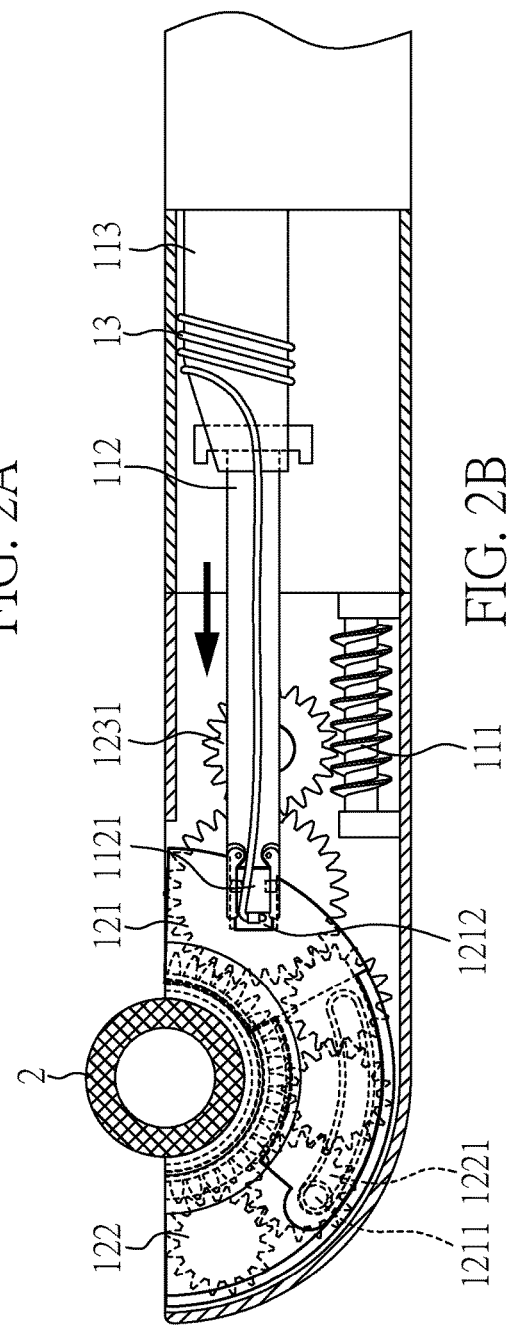

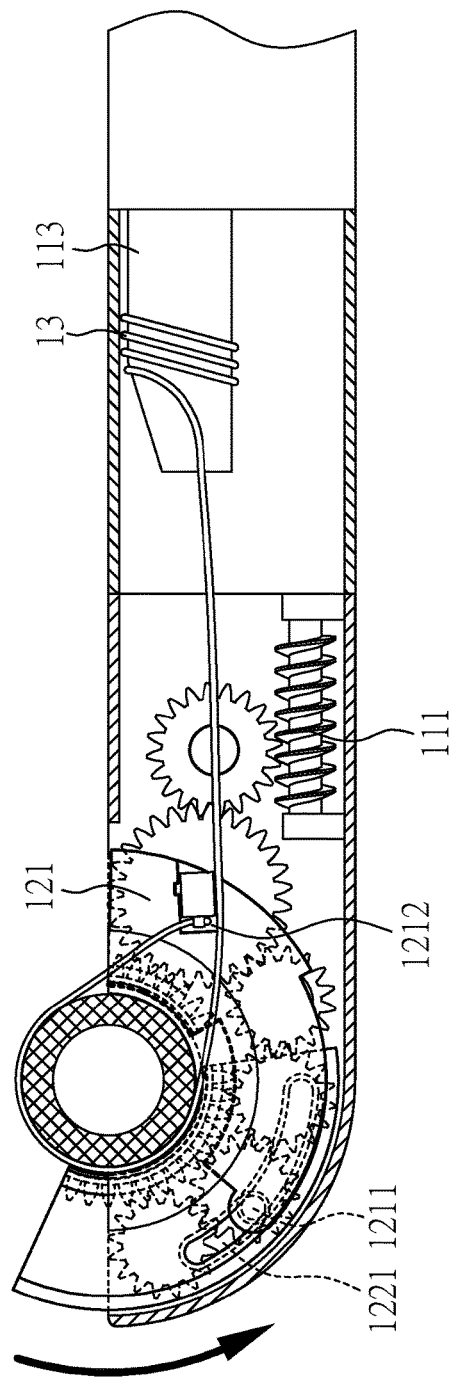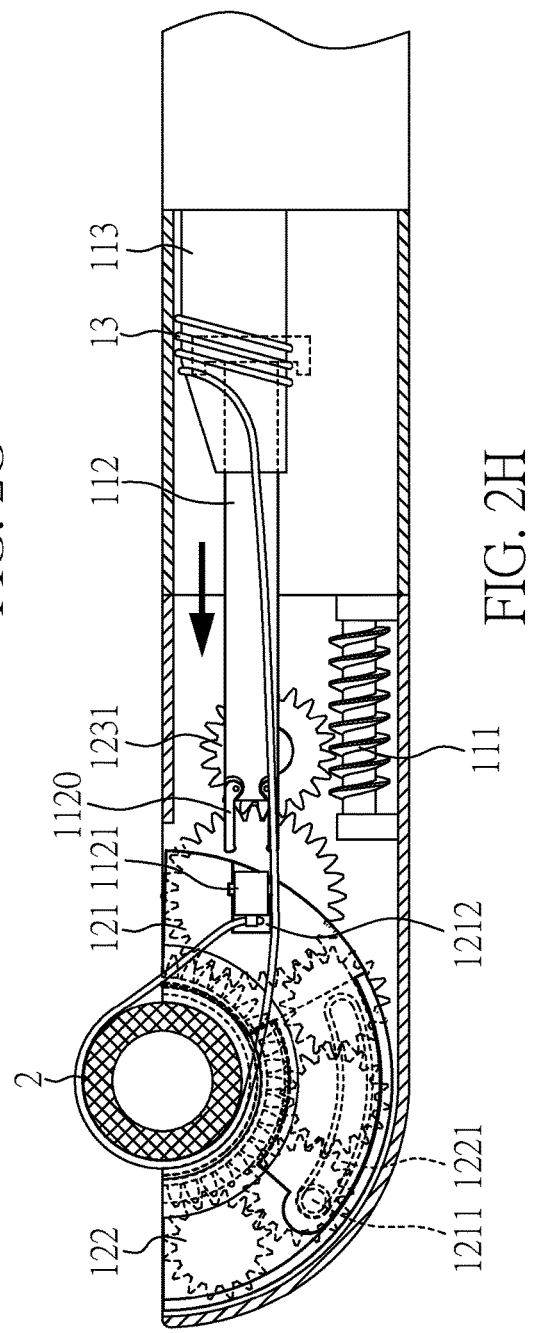
FIG. 2G
FIG. 2H

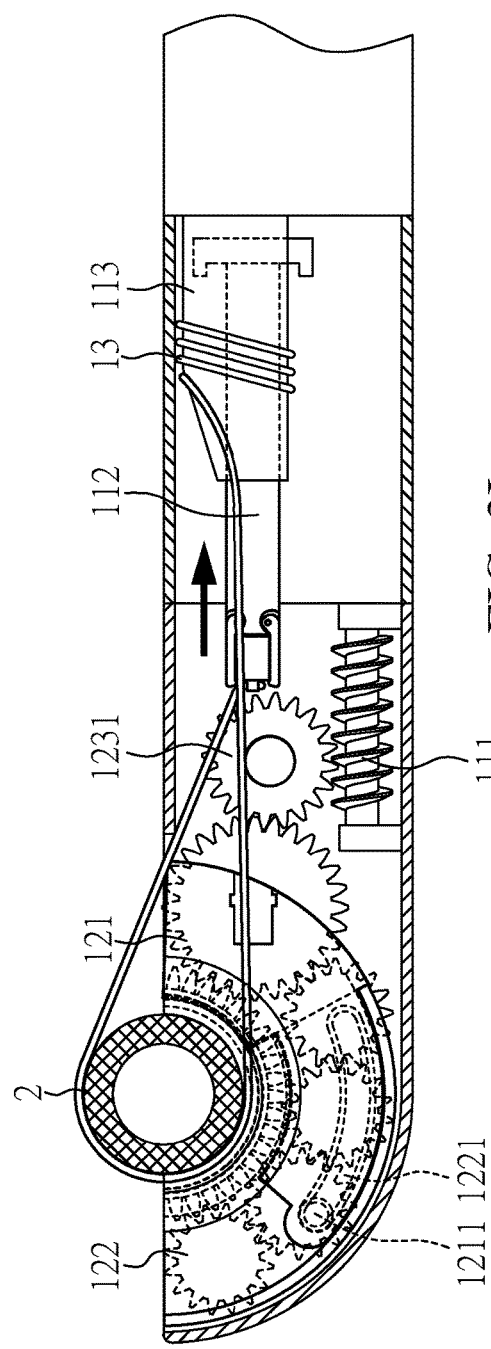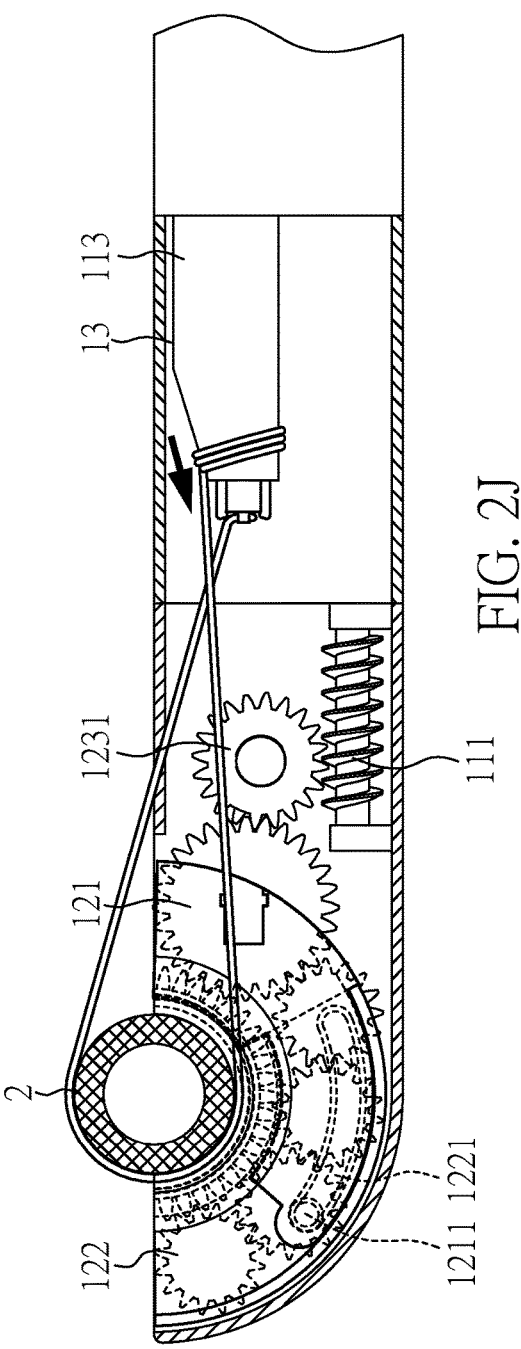

DEVICE FOR SURGICAL LIGATION

CROSS REFERENCE TO RELATED APPLICATION

This application claims the benefits of the Taiwan Patent Application Serial Number 105104824, filed on Feb. 18, 2016, the subject matter of which is incorporated herein by reference.

BACKGROUND OF THE INVENTION

1. Field of the Invention

The present invention relates to a surgical medical device. More specifically, the present invention relates to a device for surgical ligation during a surgery.

2. Description of Related Art

Ligation is a necessary procedure during a surgery. It is an important step for suturing and for stopping bleeding. Ligation quality and speed may have a great influence on operation time and post-operational healing. If the ligation quality is not good enough, knots made during ligation may loosen and slide. Wounds may then crack and bleed. The suffering and risk of patients will then be increased.

In the past, doctors usually make knots simply by hand ("hand-knotting method"). However, this method has disadvantages, such as increasing operation time and affecting the smooth flow of surgery. With advances in surgical techniques, these disadvantages become bigger issues. For example, the hand-knotting method cannot be used for minimally invasive surgery. To overcome this problem, a variety of auxiliary devices for ligation are developed to be used in such surgery. Auxiliary devices for ligation not only save time for stitching and threading, but can also be regarded as an extension of a surgical thread or an extension of a hand when the surgical thread is too short or the space is too narrow to knot. Hence, in such situation, the advantages of such auxiliary devices for ligation become very noticeable.

Currently, auxiliary devices for ligation have been widely used in surgeries. For example, during an endoscopic surgery, a laser scalpel or a harmonic scalpel is usually used for cutting or ligation. By using auxiliary devices for ligation, ligation can be completed faster than just by hands. Consequently, operation time can be shortened. However, laser scalpels are only better at stopping bleeding of small-diameter vessels. Although bipolar electrocautery scalpels are capable of stopping bleeding of large-diameter vessels, but they may also cause heat damage to surrounding tissues. Even though a subsequently improved device, named "Tissue Coagulation Instrument LigaSure™ System", can effectively reduce heat damage to surrounding tissues, the LigaSure™ system is still incapable of ligating large-diameter vessels. In addition, during a thoracoscopic surgery, titanium alloy clips or staplers are used to clamp or seal blood vessels-containing tissues. However, titanium alloy clips or staplers are foreign substances that cannot be absorbed by human body and will be retained in human body after surgery.

Hence, as mentioned above, high-energy devices, such as laser scalpels or harmonic scalpels, and stapling devices can only be used at specific surgical sites. In addition, each of these devices has some disadvantages that need to be overcame. In contrast, if a ligation is done by suturing, there is no need to purchase additional expensive devices or to learn how to use such devices. In addition, compared with the high-energy devices for ligation, suturing can easily ligate large size vessels. Moreover, accidents that happened when high-energy devices are used will not happen during suturing. Furthermore, sutures that can be absorbed by human body have been developed in recent years. Hence, the application of suturing is wider compared to that of high-energy devices or stapling devices.

Although, several teams have developed auxiliary devices for ligation by suturing; however, so far, such auxiliary devices for ligation still require the use of both hands to complete ligation. Thus, in practical situations, such devices may still affect the smooth flow of a surgery. Therefore, there is a need to develop a surgical ligation device that can overcome the aforementioned drawbacks of known auxiliary devices for ligation so that physicians can perform tubular tissue ligation in a much quicker and simpler manner.

SUMMARY OF THE INVENTION

In order to overcome the drawbacks of conventional ligation, the present invention provides a device for surgical ligation to assist tubular tissue ligations. With the device for surgical ligation of the present invention, ligation can be done in a time saving manner and can be done within a limited space automatically. The flow of surgery can then be improved as well. More specifically, the device for surgical ligation of the present invention can assist physicians to perform ligation automatically with only one single hand. The device for surgical ligation of the present invention is different from conventional ligation that needs to be performed by bare hands or needs to use auxiliary devices operated by both hands.

To achieve the aforesaid object, the present invention provides a device for surgical ligation, which is guided by a mechanical actuation mechanism to complete winding of sutures and surgical knots.

In order to allow the person having ordinary skills in the art to have a better understanding of the present invention, terms, such as "first", "second", and the likes, in the present invention are used to distinguish different elements of the same name. These terms are not intended to define and limit such elements.

In particular, the device for surgical ligation of the present invention comprises: a housing, where a pulling portion is provided therein; and an opening portion provided at one end of the housing and connected to the pulling portion, where a line delivery element is provided therein.

The line delivery element comprises: a first arc unit having a first coupling portion and a slot thereon; a second arc unit having a second coupling portion corresponding to the first coupling portion; and a gear assembly comprising a plurality of gears engaging with each other, wherein a first gear is engaged with the pulling portion while a second gear is engaged with the second arc unit.

Specifically, the first coupling portion of the first arc unit and the second coupling portion of the second arc unit are disposed correspondingly to one another and coupled to one another. The structures of the first and the second coupling portions are not limited thereto as long as the first coupling portion and the second coupling portion are able to couple to one another. The first coupling portion and the second coupling portion, for example, may respectively be: a guide rail and a guide groove, a guide groove and a guide rail, a convex part and a concave part, a concave part and a convex part, a convex part and a guide groove, a guide groove and a convex part, a guide rail and a concave part, and a concave part and a guide rail.

In the present invention, the gear assembly comprises the first gear, the second gear, and at least a third gear. These gears are engaged with each other. For example, these gears may form a gear assembly such as: a first gear, a third gear, and a second gear; a first gear, two third gears, and a second gear; a first gear, three third gears, and a second gear; a first gear, four third gears, and a second gear; a first gear, five third gears, and a second gear; and the likes. However, the invention is not limited thereto. Preferably, the gear assembly is provided on a side of the first arc unit and the second arc unit. More preferably, the second arc unit is engaged with at least the second gear of the gear assembly so that the movement of a ligating loop will be driven and guided by the gear assembly.

The pulling portion of the present invention at least comprises a first driving rod, a second driving rod, a third driving rod, and a stationary rod. However, these "rods" are not limited in the present invention. That is, the "rods" used in the present invention are not limited to any conventional rod-shaped object. Instead, any object can be used in the present invention as long as the object functions as a power transmission medium. For example, in an aspect, a combination of ropes, pulleys, and connecting rods can replace a metal rod to deliver power. Thus, such "a combination of ropes, pulleys, and connecting rods" can be regarded as an example of the "rod" in the invention.

In a preferred example of the present invention, the first driving rod may be a worm engaged with a gear of the gear assembly. In this way, a user may drive the gear assembly through controlling the first driving rod. For example, by controlling the first driving rod to rotate, the first driving rod (i.e. the worm) will drive the gear assembly to rotate as well, causing the second arc unit to rotate clockwise or counter-clockwise.

One end of the second driving rod may contain a fastener structure. The fastener structure may engage with a fixing unit where an end of a ligating loop is fixed. Hence, by controlling the second driving rod to move back and forth, the second driving rod may move the fixing unit toward the opening portion or may move the fixing unit away from the opening portion.

The fixing unit functions as a bridge for "connecting" a ligating loop with the elements/units of the device for surgical ligation of the present invention. For example, an end of a ligating loop is fixed on the fixing unit and the fixing unit is engaged with the elements/units (i.e. the slot or the fastener structure) of the device of the present invention. To ensure the fixing unit will engage with the slot or the fastener structure smoothly, the material and the structure of the fixing unit, the slot, or the fastener structure may be changed and designed correspondingly and with respect to one another. For example, in an example of the present invention, the fixing unit can be formed using an elastic material so that the fixing unit can engage with the slot and the fastener structure smoothly. The elastic material, for example, may be materials, such as rubber, plastic, or polymer. Alternatively, the slot and the fastener structure may each have a reset unit, such as a spring, to allow the fixing unit to engage with the slot and the fastener structure.

A pre-prepared ligating loop may be set on the stationary rod, and as described above, an end of the ligating loop is fixed on the fixing unit. The ligating loop may be any surgical knot widely used in the related arts and may preferably be a slipknot. However, the present invention is not limited thereto. User may use any appropriate surgical knot based on the actual situations.

In a preferred example of the present invention, after a knotting step is finished, the third driving rod may push the knotted ligating loop toward the target tubular tissue to complete a tubular tissue ligation. More specifically, after the ligating loop has been driven by the device of the present invention to loop around the target tubular tissue, the second driving rod will be driven to move toward the opening portion. Once the second driving rod engages with the fixing unit engaged with the first arc unit, the second driving rod will move the fixing unit away from the opening portion. The ligating loop on the stationary rod will move toward the opening portion and becomes knotted. The third driving rod then moves toward the opening portion and push the knotted ligating loop to the target tubular tissue to complete a tubular tissue ligation.

In an example of the present invention, the second driving rod may move (back and forth) through the stationary rod. However, in another example of the present invention, the second driving rod may not be provided in the stationary rod. In other words, the second driving rod and the stationary rod may be provided independently in different positions in the housing. Similarly, the third driving rod may be designed to move (back and forth) through the stationary rod or move (back and forth) outside of the stationary rod. However, the present invention is not limited thereto.

In other examples, in order to control the device for surgical ligation of the present invention in a more finely manner, a fourth driving rod, a fifth driving rod, and the likes may be added optionally. However, the present invention is not limited thereto.

The device for surgical ligation of the present invention may further comprise a control portion provided at an end of the housing that is different from the end of the housing connected to the opening portion. Since the control portion is connected to the pulling portion, user may control each driving rod of the pulling portion to accomplish a tubular tissue ligation.

In a preferred example of the present invention, the control portion may contain a stepper motor to control the device of the present invention to knot. In this case, the device for surgical ligation of the present invention may be designed as a hand-held device with a plurality of control buttons on its handle so that tubular tissue ligation can be achieved using one single hand.

In another example of the present invention, the device for surgical ligation of the present invention may be used with known minimally invasive surgery systems (e.g. Da Vinci system). User may control the device of the present invention directly to accomplish tubular tissue ligation, allowing the device of the present invention to be further applied in minimally invasive surgeries.

Other objects, advantages, and novel features of the present invention will become more apparent from the following detailed description when taken in conjunction with the accompanying drawings.

BRIEF DESCRIPTION OF THE DRAWINGS

FIGS. 2A to 2M are schematic views showing steps of a ligation performed by the device for surgical ligation of the present invention;

DETAILED DESCRIPTION OF THE PREFERRED EMBODIMENT

In the following disclosure, the aforesaid features of the present invention will be described in detail. However, the following examples are merely to illustrate some embodiments of the present invention so that a person having ordinary skills in the art may understand the advantages and the effects of the present invention. The present invention may also be applied and implemented in various embodiments. The details of the present disclosure may also have various modifications or changes depending on different applications without departing from the spirit of the present invention.

Example 1: Hand-Held Device for Surgical Ligation

Figure 1A:
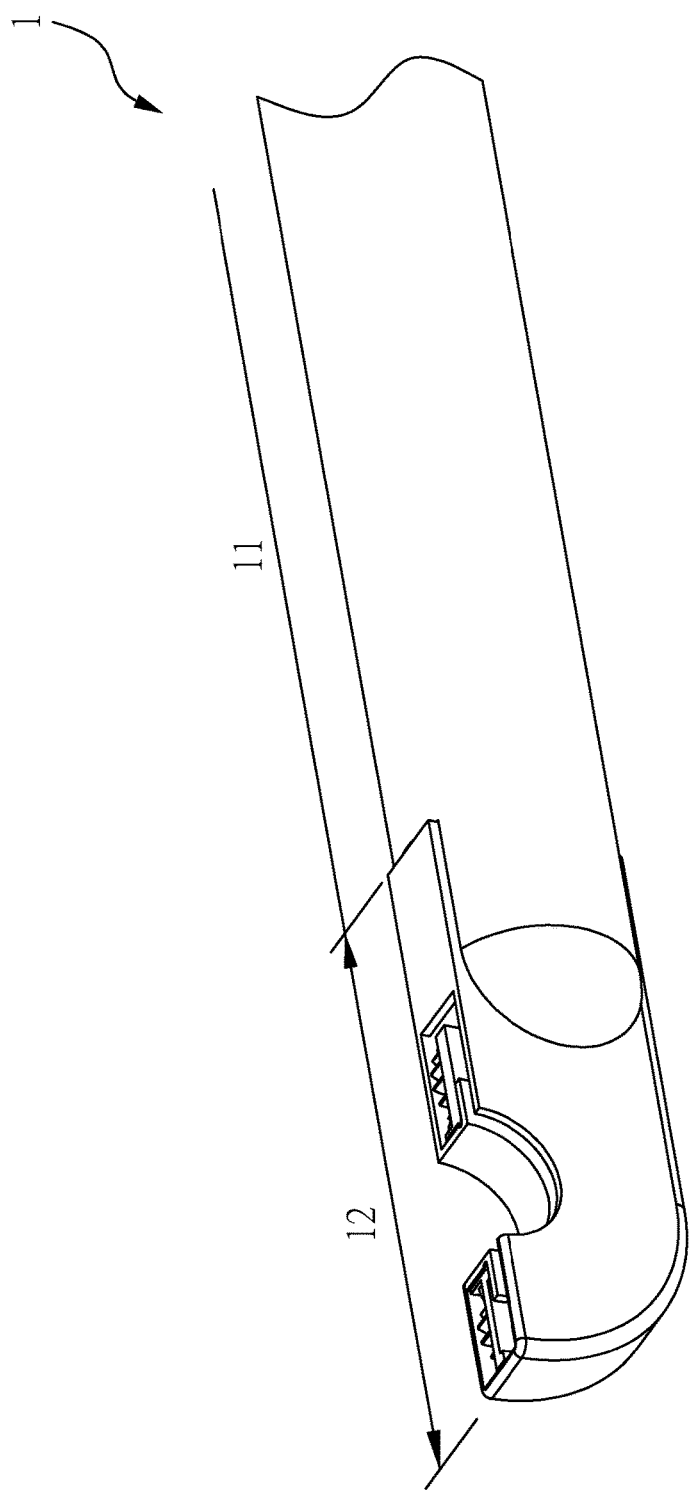
FIG. 1A is an appearance of a preferred example of the device for surgical ligation of the present invention.
Figure 1B:
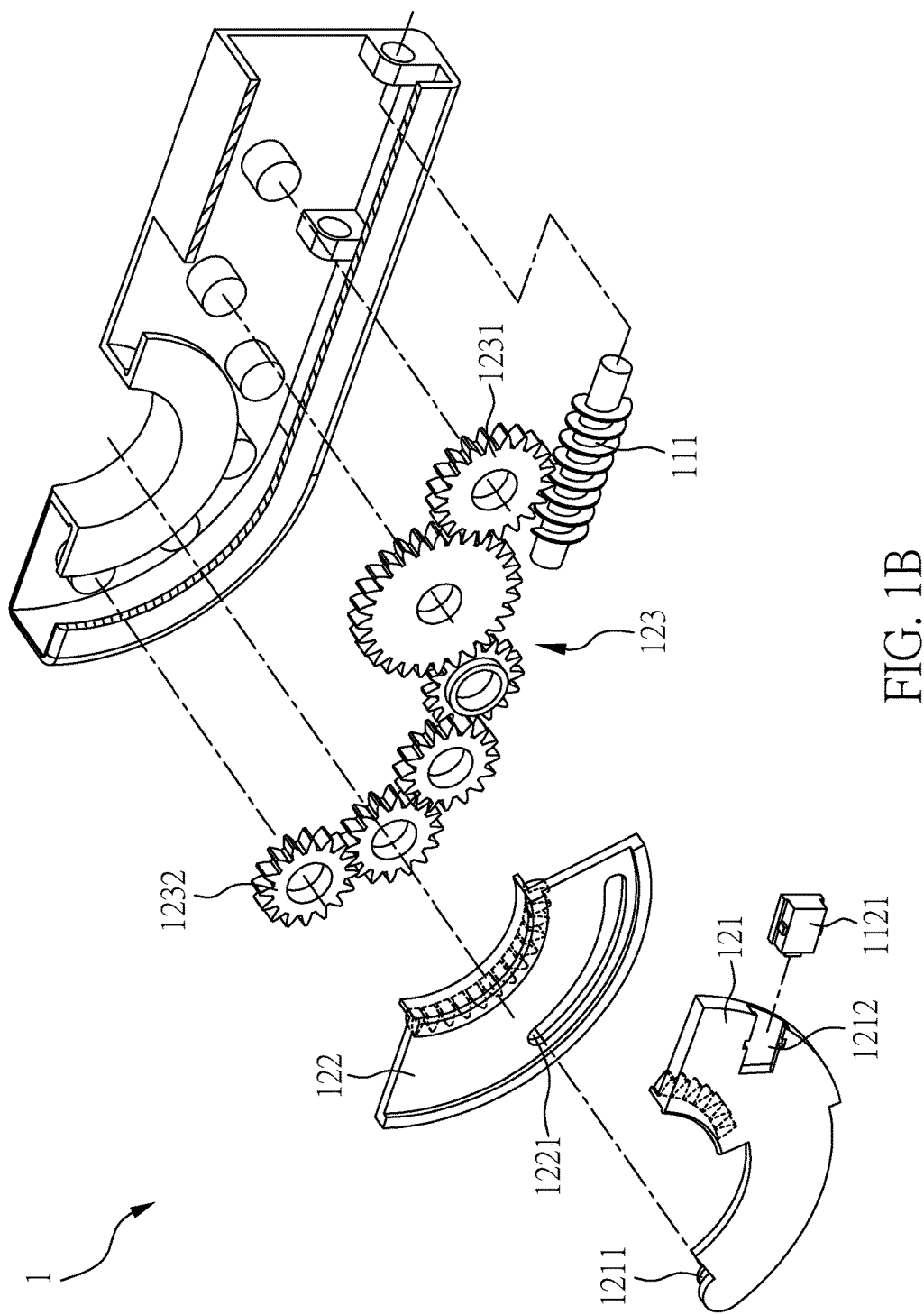
FIG. 1B is an exploded view of a preferred example of the device for surgical ligation of the present invention.

FIG. 1A is an appearance of a preferred example of the device for surgical ligation of the present invention while FIG. 1B is an exploded view of a preferred example of the device for surgical ligation of the present invention.

Referring to FIG. 1A, the device for surgical ligation 1 is divided into a housing 11 and an opening portion 12 in general.

From the exploded view of the device shown in FIG. 1B, the relationships of each element/unit in the opening portion 12 of the device for surgical ligation 1 will be further described.

The opening portion 12 is provided at an end of the housing 11 and connected to a pulling portion via a first driving rod 111 of the pulling portion. The opening portion 12 contains a line delivery element, which comprises: a first arc unit 121 having a first coupling portion 1211 and a slot 1212; a second arc unit 122 having a second coupling portion 1221, in which the second coupling portion 1221 is disposed correspondingly to the first coupling portion 1211; and a gear assembly 123 having a plurality of gears engaging with each other, in which in the gear assembly 123, a first gear 1231 is engaged with the first driving rod 111 while a second gear 1232 is engaged with the second arc unit 122. Furthermore, there are a plurality of additional third gears disposed between the first gear 1231 and the second gear 1232. In more detail, the first arc unit 121 connects to the second arc unit 122 via the first coupling portion 1211 and the second coupling portion 1221. The second arc unit 122 engaged with the gear assembly 123 may drive the first arc unit 121 to move via gear actuation.

Figure 1C:
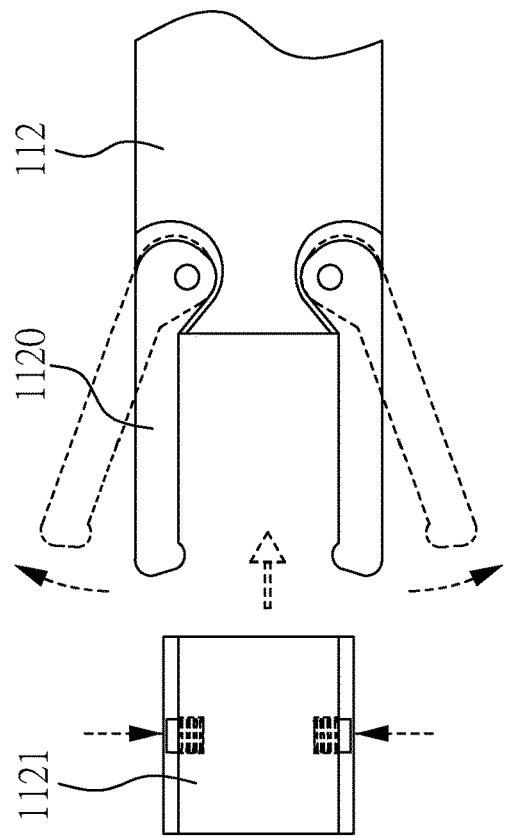
FIG. 1C is an enlarged view of a fixing unit and a fastener structure of an example of the device for surgical ligation of the present invention.
Figure 1D:
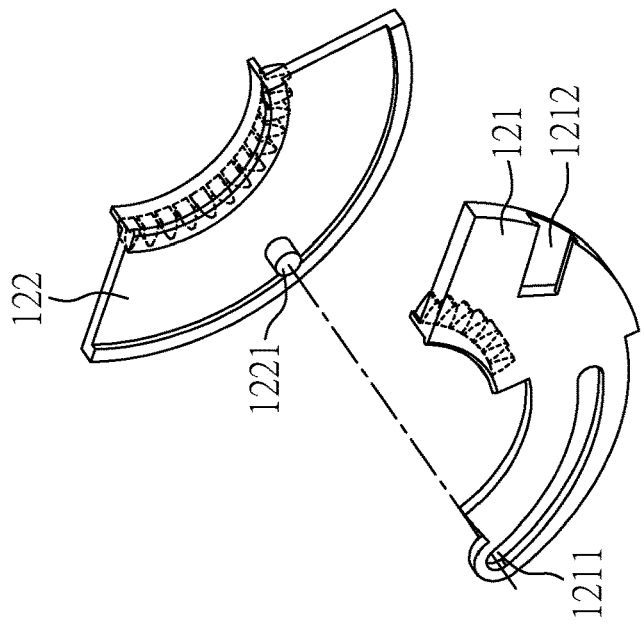
FIG. 1D shows a first arc unit and a second arc unit of an example of the device for surgical ligation of the present invention.

In the present invention, as long as the first coupling portion 1211 and the second coupling portion 1221 are correspondingly disposed and connected to each other, the structures of the first coupling portion 1211 and the second coupling portion 1221 are not limited to the structures shown in FIG. 1B. As shown in FIG. 1B, the first coupling portion 1211 may be a convex part while the second coupling portion 1221 may be a guide groove. However, the first coupling portion 1211 and the second coupling portion 1221 can be in other structures as well. For example, FIG. 1D shows other structures of the first coupling portion 1211 and the second coupling portion 1221. As shown in FIG. 1D, the first coupling portion 1211 is a guide groove while the second coupling portion 1221 is a convex part. However, as emphasized above, as long as the first coupling portion 1211 and the second coupling portion 1221 can connect smoothly, the structures of the first coupling portion 1211 and the second coupling portion 1221 are not limited.

Next, the operation of the device for surgical ligation of the present invention will be described through FIGS. 2A to 2M.

FIG. 2A is a sectional diagram showing the device for surgical ligation of the present invention in a standby status. First, the recess part of the opening portion 12 is disposed correspondingly to a vessel 2 to be ligated. As shown in FIG. 2A, in a standby status, the first coupling portion 1211 of the first arc unit 121 connects to the second coupling portion 1221 of the second arc unit 122. The gear assembly is disposed on a side of the first arc unit 121 and the second arc unit 122. In the gear assembly, at least one gear is engaged with the second arc unit 122 and another gear 1231 of the gear assembly is engaged with the first driving rod 111 of the pulling portion.

The pulling portion is disposed within the housing 11. As shown in FIG. 2A, in addition to the first driving rod 111, the pulling portion further comprises a second driving rod 112, a third driving rod (not shown), and a stationary rod 113. The second driving rod 112 has a fastener structure 1120 at one of its end. The fastener structure 1120 is engaged with a fixing unit 1121. An end of a ligating loop 13 is fixed on the fixing unit 1121. The ligating loop 13 formed by a surgical thread is set on the stationary rod 113. The first driving rod 111, the second driving rod 112, and the third driving rod are connected to an external driving device such as a motor or other mechanical power systems. The said external driving device provides power to drive the following actions.

To begin ligation, as shown in FIG. 2B, the second driving rod 112 first moves toward the first arc unit 121 (the direction indicated by the arrow). The fixing unit 1121 originally fixed at an end of the second driving rod 112 then engages with the slot 1212 of the first arc unit 121.

Figure 2C:
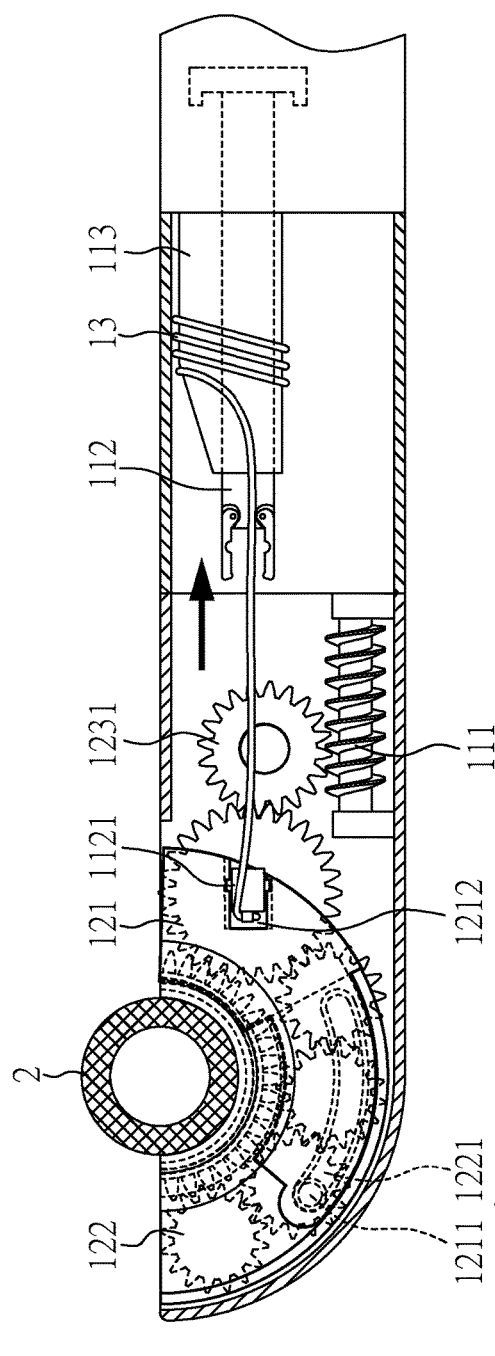
Figure 2D:
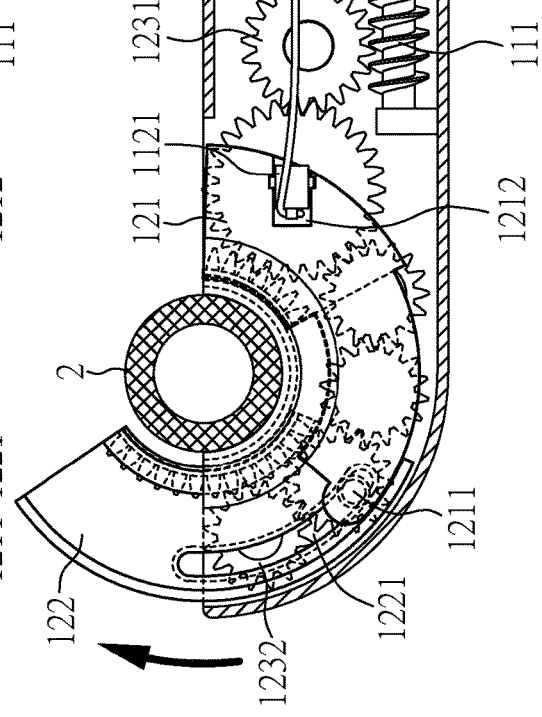

When the second driving rod 112 moves away from the opening portion (as indicated by the arrow in FIG. 2C), the first driving rod 111 is rotated to drive the first gear 1231 (as shown in FIG. 2D). The gear assembly is then actuated. The second gear 1232 engaged with the second arc unit 122 then drives the second arc unit 122 in a clockwise direction.

It should be noted that, in the present embodiment, the second arc unit 122 is rotated clockwise to make the ligating loop 13 to loop around the blood vessel 2. However, in another embodiment, depending on the blood vessel 2 and the device for surgical ligation 1 of the present invention, the second arc unit 122 may rotate counter-clockwise to make the ligating loop 13 to loop around the blood vessel 2.

Figure 2E:
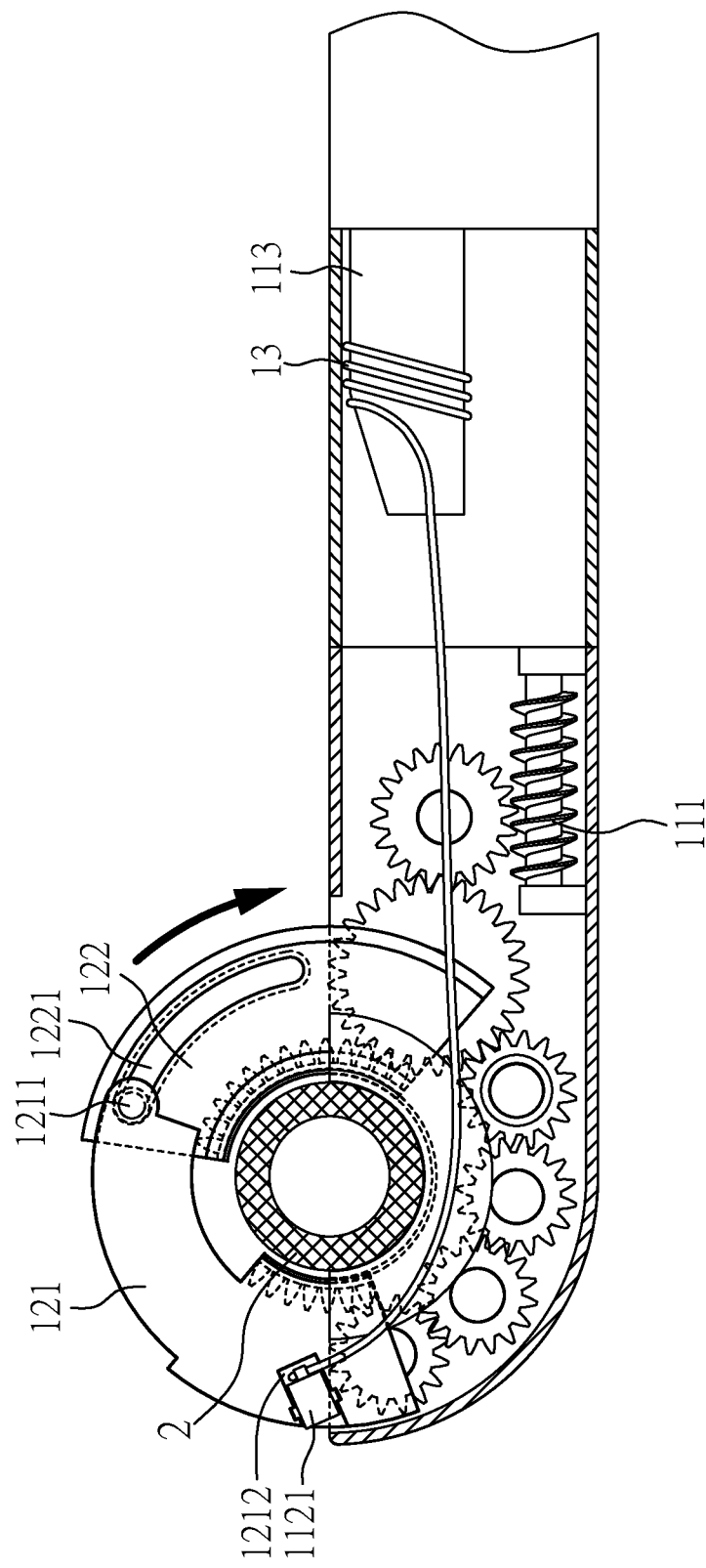

Next, as shown in FIG. 2E, the second arc unit 122 drives the first arc unit 121 to move in the same direction (clockwise), making the fixing unit 1121 engaged with the slot 1212 of the first arc unit 121 to move as well. The fixing unit 1121 where an end of the ligating loop 13 is fixed begins to surround the target vessel 2 (as indicated by the arrow).

Figure 2F:
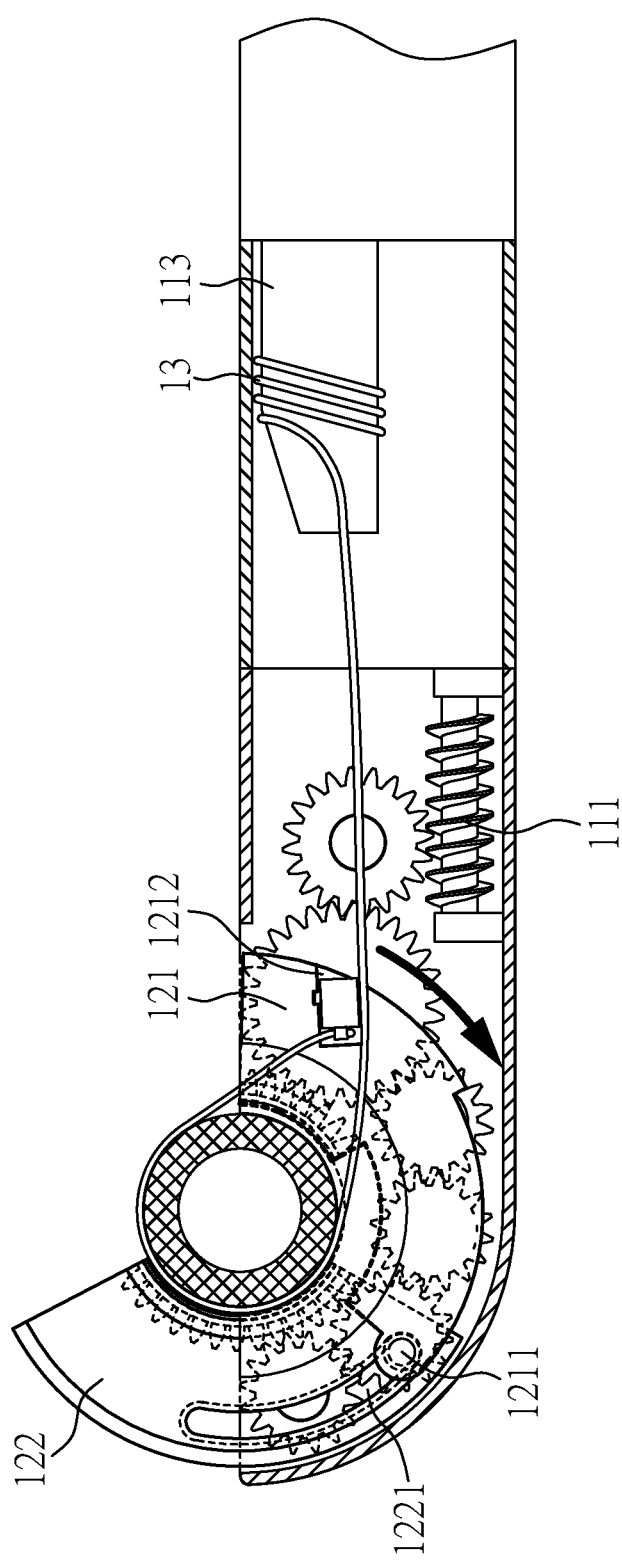

As shown in FIG. 2F, when the fixing unit 1121 has been driven to rotate in a clockwise direction for one complete round and return to the original position, the target vessel 2 is completely surrounded by the ligating loop 13. As shown in FIG. 2G, by controlling the rotation of first driving rod 111 to drive the clockwise rotation of the first gear 1231, the gear assembly makes the second arc unit 122 to rotate counterclockwise. The second arc unit 122 then moves back to the original standby position as shown in FIG. 2A (as indicated by the arrow).

Next, as shown in FIG. 2H, the second driving rod 112 moves toward the opening portion 12 again. The fixing unit 1121 engaged with the first arc unit 121 then engages with the fastener structure 1120 located at an end of the second driving rod 112 again.

To allow the fixing unit 1121 to engage with the slot 1212 or the fastener structure 1120 smoothly, the fixing unit 1121, the slot 1212, or the fastener structure 1120 may be formed using specific materials or designed to have specific structures. In an example of the present invention, as shown in FIGS. 1B and 1C, the fixing unit 1121 may contain at least one reset unit, such as a spring. In this way, when the fixing unit 1121 combines with the fastener structure 1120, the fastener structure 1120 can clamp the fixing unit 1121 very tightly by pressing down the reset units of the fixing unit 1121 (as indicated by the arrows in FIG. 1C). After the fastener structure 1120 pushes the fixing unit 1121 into the slot 1212, the fastener structure 1120 unclamps the fixing unit 1121. The reset units pop out and allow the fixing unit 1121 to engage with the slot 1212. However, the present invention is not limited thereto. In another example, the fixing unit 1121 may be formed by any known elastic material, such as rubber, plastic, or other polymer materials, so that the fixing unit 1121 can engage with the slot 1212 and the fastener structure 1120 smoothly.

Figure 2K:
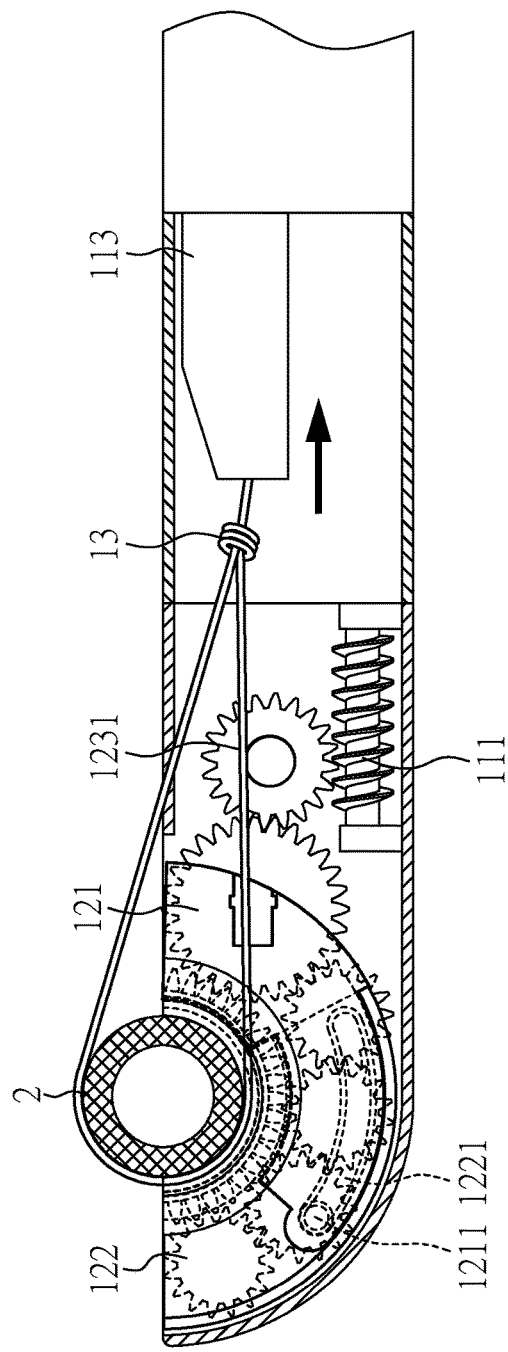

As shown in FIG. 2I, after the fastener structure 1120, which is located at an end of the second driving rod 112, engages with the fixing unit 1121 again, the second driving rod 112 moves away from the opening portion 12 (as indicated by the arrow). At the same time, one end of the ligating loop 13 is pulled away from the opening portion 12. At this time, as shown in FIG. 2J, the ligating loop 13, which originally sets on the stationary rod 113, moves toward the opening portion 12 and makes the ligating loop 13 to form a knot (FIG. 2K).

Figure 2L:
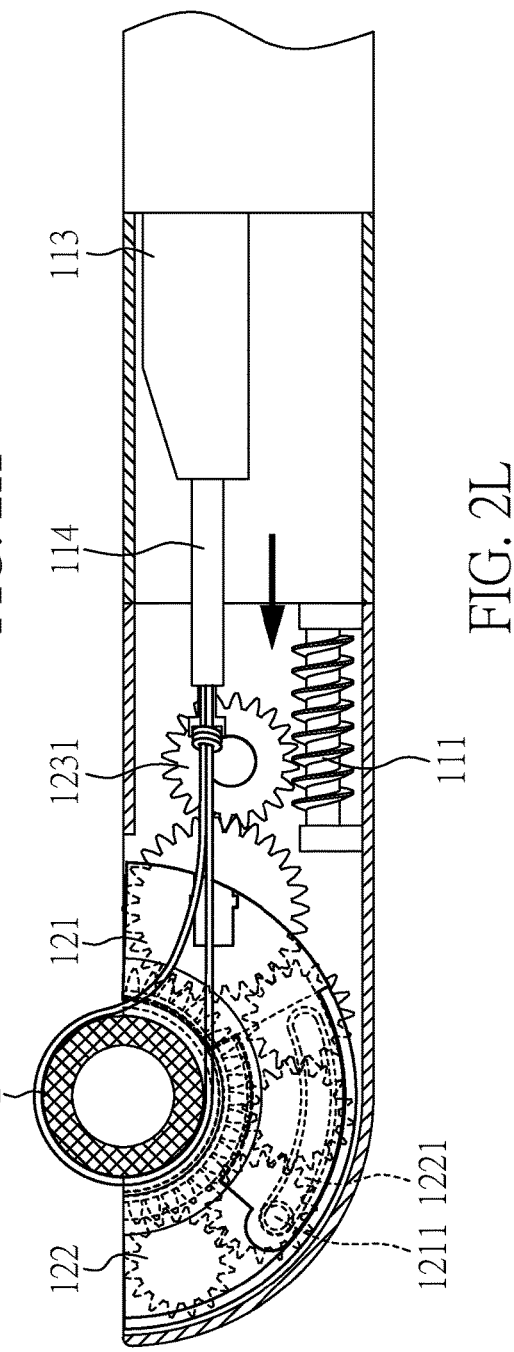
Figure 2M:
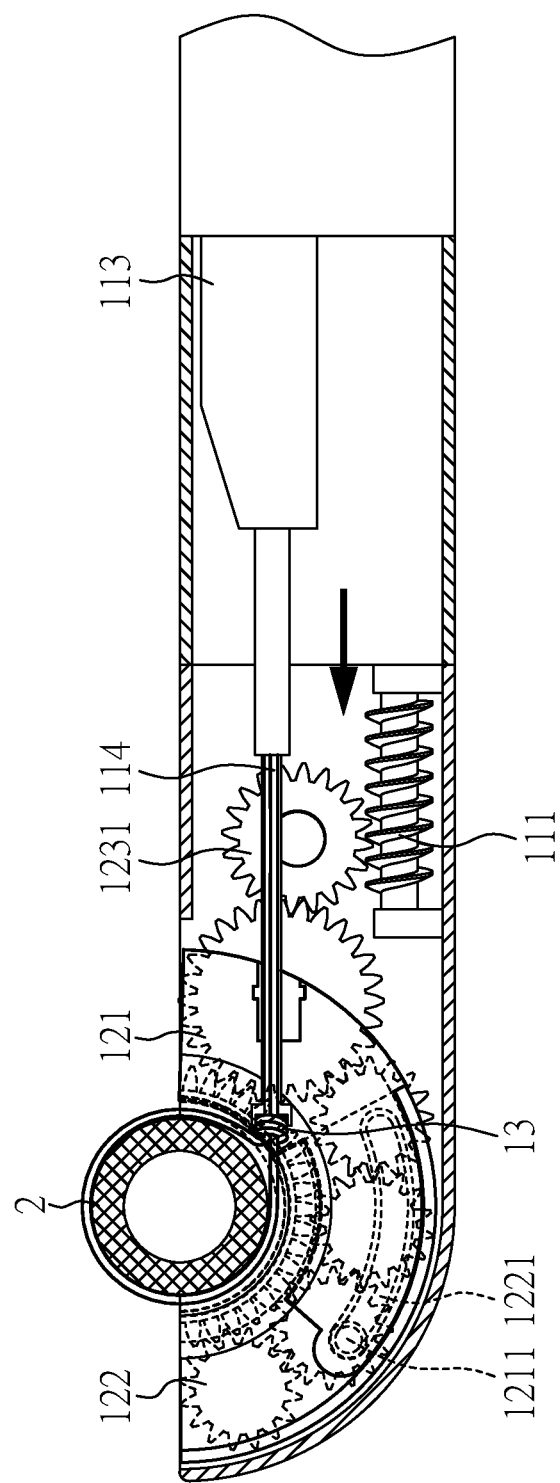

Finally, as shown in FIG. 2L, the third driving rod 114 pushes the knot of the ligating loop 13 toward the opening portion 12 to complete the ligation of the vessel 2.

Figure 3:
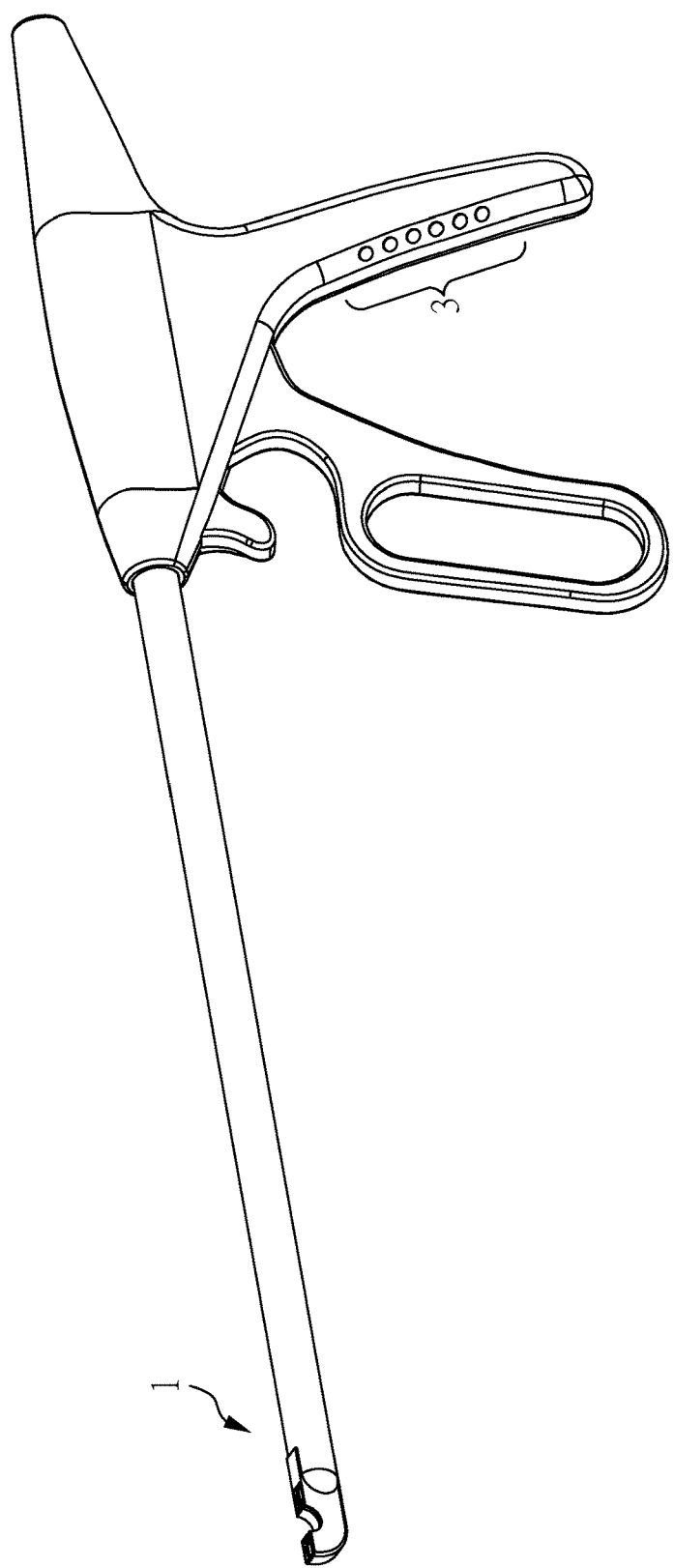
FIG. 3 shows a preferred example of a hand-held device for surgical ligation of the present invention.

As shown in FIG. 3, the device for surgical ligation 1 described above is a hand-held device for surgical ligation. The device further comprises a control portion, which is provided at an end of the housing different from the end of the housing where the opening portion is provided. Since the control portion, which contains a stepper motor, is connected to the pulling portion (not shown), user may control the moving direction of each driving rod of the pulling portion through a plurality of control buttons on the handgrip. Ligation can then be completed simply by a single hand.

Example 2: Da Vinci Surgical System

With 3D stereoscopic ultra high resolution visual images and mechanical arms that mimic human wrists and joints, the Da Vinci Surgical System significantly enhances the flexibility and accuracy of a surgery. Together with control systems that are precise and accurate as well as having intuitive reaction, the Da Vinci Surgical System has been widely used in surgeries, such as urology, gynecology, general surgery, colorectal surgery, cardiac surgery, thoracic surgery, otolaryngology—head and neck surgery.

Figure 4:
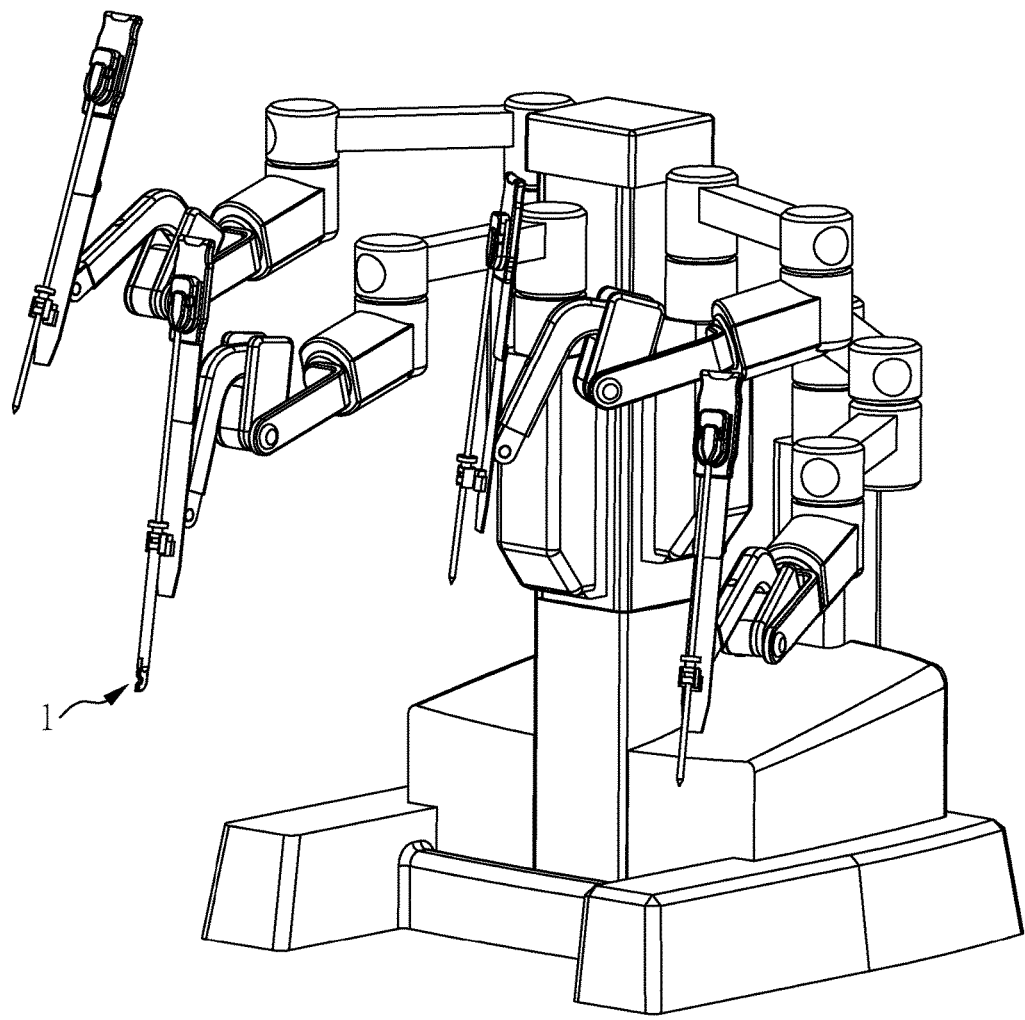
FIG. 4 is shows a preferred example of a combination of the device for surgical ligation of the present invention and the Da Vinci system.

As shown in FIG. 4, in an example of the present invention, the device for surgical ligation 1 of the present invention may be mounted on a mechanical arm of the Da Vinci Surgical System. In this example, the ligation performed by the device for surgical ligation 1 is the same as that described in Example 1. Thus, the steps of the ligation performed will not repeat here again. In the present example, a chief surgeon may control the device for surgical ligation 1 of the present invention at the main station to complete ligation. Hence, the device for surgical ligation 1 of the present invention may be further used to perform a ligation during a minimally invasive surgery.

Clearly, the device for surgical ligation of the present invention may be used optionally with any known surgical device being widely used currently. By controlling the movement of the driving rods as well as the actuation of the gear assembly, ligation can be completed in a simple manner. It should be noted that the driving rods of the present invention are not limited to conventional "rods", but may be a combination of other driving apparatuses and connecting rods. In an example of the present invention, a driving rod may comprise, for example, ropes, but the present invention is not limited thereto.

Although the present invention has been explained in relation to its preferred embodiments, it is to be understood that many other possible modifications and variations can be made without departing from the spirit and scope of the present invention as hereinafter claimed.

What is claimed is:

1. A device for surgical ligation, comprising:
    a housing, where a pulling portion is provided therein, the pulling portion comprising a first driving rod, a second driving rod, a third driving rod, and a stationary rod; and
    an opening portion provided at one end of the housing and connected to the pulling portion, where a line delivery element is provided therein;
    wherein the line delivery element comprises:
    a first arc unit having a first coupling portion and a slot thereon;
    a second arc unit having a second coupling portion corresponding to the first coupling portion, wherein the first coupling portion and the second coupling portion are coupled to one another; and
    a gear assembly comprising a plurality of gears engaging with each other, wherein a first gear is engaged with the pulling portion while a second gear is engaged with the second arc unit;
    wherein the second arc unit engaged with the second gear is configured to drive the first arc unit to move via gear actuation.

2. The device for surgical ligation as claimed in claim 1, wherein the gear assembly is provided on a side of the first arc unit and the second arc unit.

3. The device for surgical ligation as claimed in claim 1, wherein the first coupling portion and the second coupling portion are respectively: a guide rail and a guide groove, a guide groove and a guide rail, a convex part and a concave part, a concave part and a convex part, a convex part and a guide groove, a guide groove and a convex part, a guide rail and a concave part, or a concave part and a guide rail.

4. The device for surgical ligation as claimed in claim 1, wherein the first driving rod is a worm and the worm is engaged with the first gear of the gear assembly.

5. The device for surgical ligation as claimed in claim 1, wherein an end of the second driving rod has a fastener structure.

6. The device for surgical ligation as claimed in claim 5, wherein both the slot and the fastener structure contain one reset unit, wherein the reset unit is a spring.

7. The device for surgical ligation as claimed in claim 1, wherein the second driving rod is moving through the stationary rod.

8. The device for surgical ligation as claimed in claim 1, wherein the third driving rod is moving through the stationary rod.

9. The device for surgical ligation as claimed in claim 1, wherein a ligating loop sets on the stationary rod, and an end of the ligating loop is fixed on a fixing unit.

10. The device for surgical ligation as claimed in claim 9, wherein the fixing unit is formed of an elastic material.

11. The device for surgical ligation as claimed in claim 1, further comprises a control portion provided at an end of the housing that is different from the end of the housing where the opening portion is provided, and the control portion connects to the pulling portion.

12. The device for surgical ligation as claimed in claim 11, wherein the control portion further contains a stepper motor.

\* \* \* \* \*